United States Patent
Warmflash et al.

(10) Patent No.: US 10,648,042 B1
(45) Date of Patent: May 12, 2020

(54) ENGINEERED SECRETED REPORTERS OF CELLULAR PROCESSES

(71) Applicants: Aryeh Warmflash, Houston, TX (US); Kinshuk Mitra, Houston, TX (US)

(72) Inventors: Aryeh Warmflash, Houston, TX (US); Kinshuk Mitra, Houston, TX (US)

( * ) Notice: Subject to any disclaimer, the term of this patent is extended or adjusted under 35 U.S.C. 154(b) by 318 days.

(21) Appl. No.: 15/604,521

(22) Filed: May 24, 2017

Related U.S. Application Data

(60) Provisional application No. 62/340,873, filed on May 24, 2016.

(51) Int. Cl.
*C12Q 1/6897* (2018.01)
*A01K 67/027* (2006.01)

(52) U.S. Cl.
CPC ........ *C12Q 1/6897* (2013.01); *A01K 67/0275* (2013.01); *A01K 2217/052* (2013.01); *C12Q 2600/158* (2013.01); *C12Q 2600/178* (2013.01)

(58) Field of Classification Search
None
See application file for complete search history.

(56) References Cited

PUBLICATIONS

Ronald, et al. Artificial MicroRNAs as Novel Secreted Reporters for Cell Monitoring in Living Subjects. PLoS One v.11(7): e0159369. (Year: 2016).*

Bovenberg, M.S.S., et al. "Multiplex blood reporters for simultaneous monitoring of cellular processes." Analytical Chemistry 85(21): 10205-10210 (2013).

Chen, X., et al., "Characterization of microRNAs in serum: a novel class of biomarkers for diagnosis of cancer and other diseases," Cell Research 18:997-1006 (2008).

Esvelt, K.M., and Harris H.W. "Genome-scale engineering for systems and synthetic biology." Molecular Systems Biology 9: 641 (2013).

Fellmann, C., et al. "An optimized microRNA backbone for effective single-copy RNAi." Cell Reports 5(6):1704-1713 (2013).

Gonzalez-Martin, A., et al., "The microRNA miR-148a functions as a critical regulator of B cell tolerance and autoimmunity," Nature Immunology 17(4): 433-442 (2016).

Heneghan H.M., et al., "Systemic miRNA-195 Differentiates Breast Cancer from Other Malignancies and Is a Potential Biomarker for Detecting Noninvasive and Early Stage Disease," The Oncologist 15:673-682 (2010).

Maeder, M.L., and Gersbach ,C.A. "Genome Editing Technologies for Gene and Cell Therapy." Molecular Therapy 24(3): 430-436 (2016).

Qiu, L., et al. "A construct with fluorescent indicators for conditional expression of miRNA." BMC Biotechnology 8: 77 (2008).

Shapiro, M.G. et al. "Genetically encoded reporters for hyperpolarized xenon magnetic resonance imaging." Nature Chemistry 6: 629-634 (2014).

Shu, J., et al., "Computational Characterization of Exogenous MicroRNAs that Can Be Transferred into Human Circulation," PLoS One 10(11): e0140587 (2015).

Villarroya-Beltri, Carolina, et al. "Sumoylated hnRNPA2B1 controls the sorting of miRNAs into exosomes through binding to specific motifs." Nature Communications 4 (2013).

* cited by examiner

*Primary Examiner* — Jennifer Pitrak McDonald
(74) *Attorney, Agent, or Firm* — Boulware & Valoir

(57) ABSTRACT

A method of determining an amount of transcript in a living organism, the method requiring editing a genome of a living organism to include a DNA copy of a unique microRNA barcode downstream of a promoter of a transcript to be measured, such that expression of that transcript includes expression of said microRNA barcode. Then, one collects secretions from said living organism and measures a level of said transcript by measuring the amount of the unique microRNA barcode present in those secretions. Cells, tissue and animals containing such barcodes are also included.

19 Claims, 10 Drawing Sheets

Specification includes a Sequence Listing.

FIGURE 3
FIGURE 4
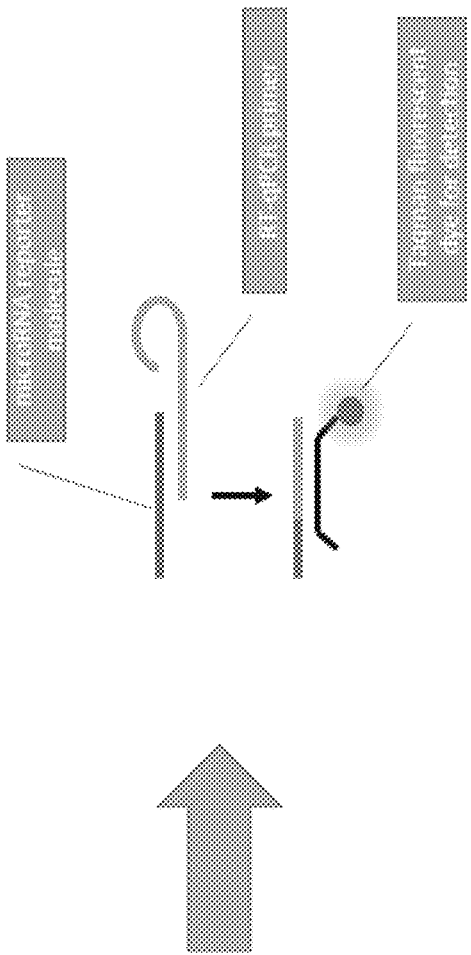
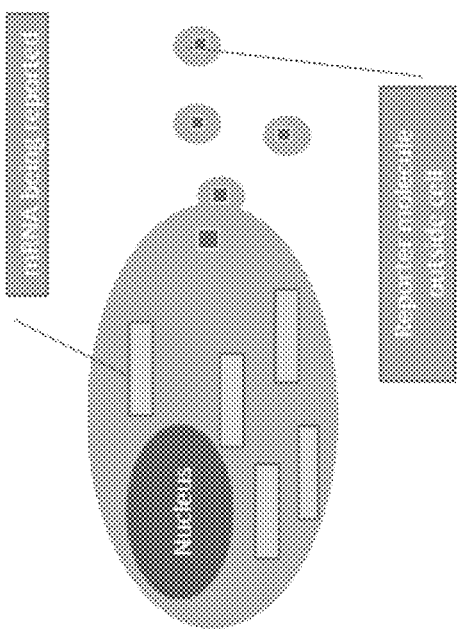

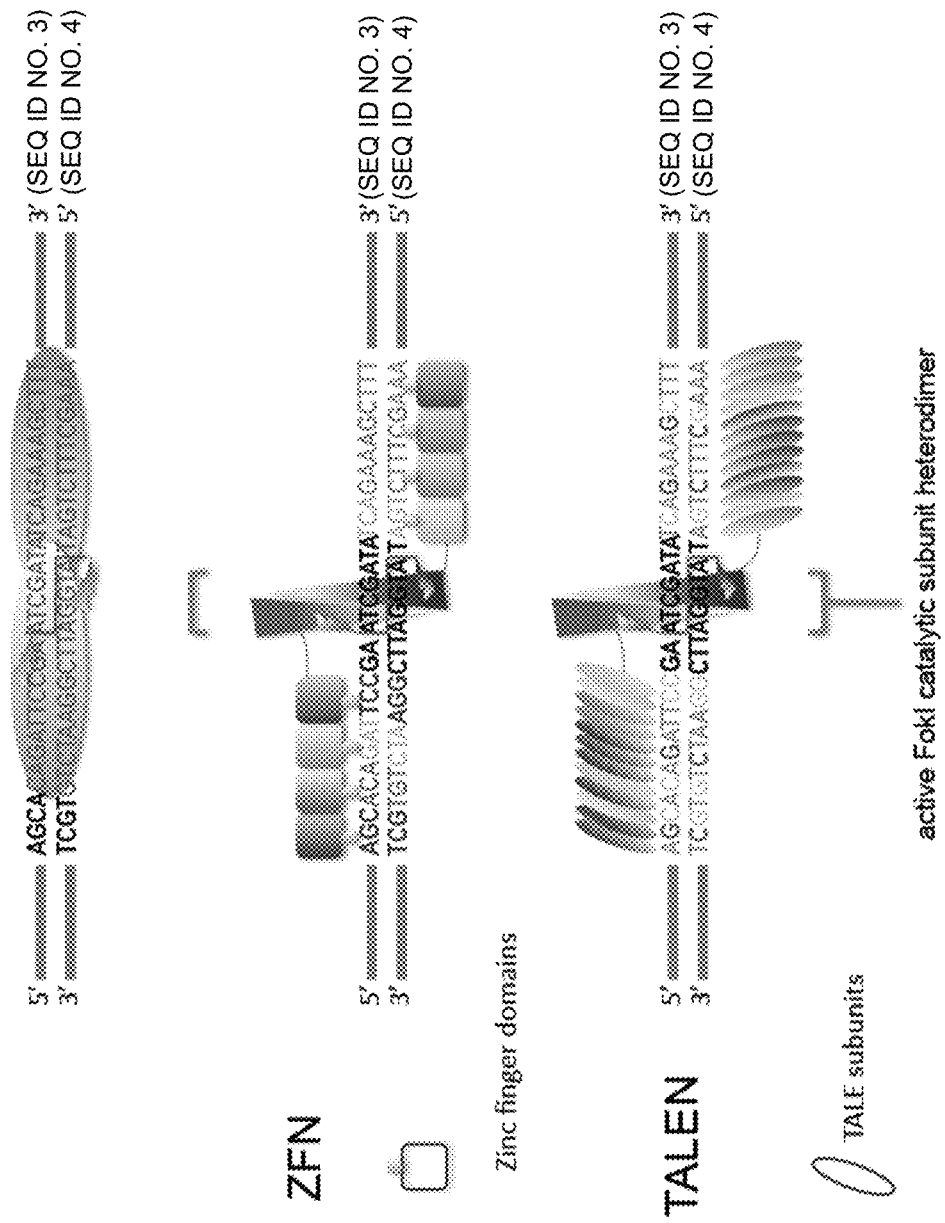

FIGURE 9

| Organisms | Genes | Methods of ZFN development |
|---|---|---|
| Gene disruption | | |
| Fruitflies | yellow, rosy, brown | Modular assembly |
| Zebrafish | kdr | Bacteria one-hybrid |
| | golden, no tail | Two-finger modules |
| | tf2, dzt, telomerase | OPEN |
| Human T cells | CCR5 | Two-finger modules |
| Rats | Rab38, IgM, IDrg | Two-finger modules |
| Gene correction | | |
| Tobacco | SuRA, SuRB | OPEN |
| Arabidopsis thaliana | ABI4, KU80 | Modular assembly |
| | TT4, ADH1 | OPEN |
| Fruitflies | yellow, rosy, coilin, pask | Modular assembly |
| Human T cells | IL2RG | Two-finger modules |
| Gene addition | | |
| Tobacco | Chitinase | Two-finger modules |
| Zea mays | Ipk1, Zein protein 15 | Two-finger modules |
| Human ES cells | IL2RG, CCR5 | Two-finger modules |
| | PIGA | OPEN |

ENGINEERED SECRETED REPORTERS OF CELLULAR PROCESSES

PRIOR RELATED APPLICATIONS

This application claims priority to U.S. Application Ser. No. 62/340,873, filed May 24, 2016, and incorporated by reference herein in its entirety for all purposes.

FEDERALLY SPONSORED RESEARCH STATEMENT

Not applicable.

FIELD OF THE DISCLOSURE

The disclosure generally relates to methods of labeling to track the production of transcripts by living cells.

BACKGROUND OF THE DISCLOSURE

There is a great need in the art for a method of non-destructively tracking RNA production both in vitro and in vivo. For example, in stem cell or gene therapies, a cell is used in the therapy, and it would be very beneficial to know whether that cell expresses particular mRNAs as a measure of whether it has properly differentiated. This would be a very useful tool as we continue to develop cell-based therapies or understand cellular pathologies.

Thus, what is needed in the art are better methods of monitoring gene expression in cells in an in vivo or ex vivo environment. The ideal method would provide good sensitivity, be compatible with patient use, as well as allow the measurement of multiple transcripts at the same time. This application addresses one or more or those needs.

SUMMARY OF THE DISCLOSURE

Current methods to detect cellular transcripts non-invasively suffer from poor sensitivity and limited ability to track the expression of multiple transcripts. Our system allows for detection of transcripts with high sensitivity because of the ability to amplify nucleic acids via PCR. Our system also can also be optimized to ensure minimal interaction with the biological context as nucleic acids can be pre-selected for minimal complementarity to endogenous genes in the host species. More importantly, compared to current cell-free DNA or RNA sequencing methods, our technology does not require cell lysis to measure transcripts, but rather measures the transcript levels in living cells that secrete the barcodes. Thus, our methods are compatible with living systems, and even whole animals or human patients.

The features considered to be novel include:

1. The use of genome engineering tools to express microRNA molecules as barcodes or reporters of cellular transcription.
2. The design of synthetic microRNA molecules that do not serve the process of inhibiting transcription, but rather are reporting on gene expression.
3. The use and modification of endogenous microRNA processing machineries to ensure secretion of said microRNA barcodes.
4. The detection of RNA barcodes in vesicular bodies.

The methodology described herein allows for the measurement of select RNA transcripts being produced by cells by non-invasive measurement of the cellular secretions. The method utilizes genome-editing technology to specifically change or "edit" the genomes of cells. The cells are edited to insert a microRNA into the locus of the target gene of interest so that it is transcribed along with the target.

The microRNA or "miRNA" consists of a barcode of DNA sequence that is absent from the host genome, as well as containing the necessary sequence(s) for miRNA processing by the cellular machinery. During RNA translation, the promoter for the marker gene will transcribe the target gene and the microRNA. The microRNA will be processed by the endogenous cellular machinery into a mature microRNA (miRNA) sequence, which is the barcode. These synthetic microRNAs will lack endogenous targets and thus cannot serve the usual function of modulating transcription. Instead, they are packaged into cellular vesicles via endogenous pathways and secreted from the cell. The secreted vesicles can then be purified and the miRNA barcodes detected and quantified via RT-qPCR or sequencing or other methods.

Both basic biological research and applied biotechnology applications have an immediate need to non-invasively and non-destructively measure the transcripts produced by cells. Experiments can be performed over multiple time points without sacrificing the sample and therapeutic cells can be queried for functional state without invasive procedures. Conditional production of fluorescent proteins is one solution, but there are a limited number of proteins with distinguishable fluorescent spectra. In addition, imaging through the depth of human or mouse tissue requires non-optical technologies. Protein-based secreted reporters have been used in the past, but are notoriously difficult to detect, because proteins cannot be amplified prior to detection.

We solve these problems by utilizing small nucleic acid barcodes that are secreted via exosomes. Cells can be made to constitutively express these barcodes to report on their presence or genome editing technologies are used to place microRNA barcodes into relevant endogenous loci, while exosomal secretion provide a means for nondestructively separating the microRNA barcodes from the cells to be detected.

Immediate applications include leveraging the exceptional capability of non-invasive multi-parameter transcript detection capability in drug development, research, tissue engineering, and biomanufacturing. Examples include use of modified cells in mouse models for generating better cancer drugs. Oncoproteins or key potential proteins for drug development could have a miRNA barcode appended at the genomic level. In such a manner, the effect of drug pressure and chronological disease development could be studied to ascertain if and how resistance to therapy grows.

Another potential use is in scaffold design for better tissue engineered products. Tissue engineers currently lack the means to assess the functionally of a scaffold in guiding development of the tissue engineered product whether in vitro or following implantation in an organism. We can monitor markers that specify particular cell fates to ascertain if the development of the tissue engineered product is in line with established protocols.

Developmental biologists may also use our technology to study expression of transcripts during embryogenesis and tissue development in micropatterns or Petri dishes without sacrificing the samples. This would allow for a better chronological understanding of the developmental process.

For biomanufacturing of pure cells, barcodes could be knocked in upstream of marker mRNA molecules whose production would be an indicator of developing impurity amongst the cells. For example, to check induced pluripotent stem cells (iPSCs), purity barcodes could be knocked in downstream of differentiation markers, which should not be expressed in iPSCs. To detect nearly all possible unwanted cells fates, one could use markers of each of the three differentiated germ layers, such as barcodes that report on Brachyury for mesoderm, Sox17 for endoderm, and Pax6 for ectoderm. Detection of these barcodes in the bioreactor would indicate the presence of unwanted differentiated cells, identify the type of these cells, and allow for optimization of cell media to reduce the developing impurity.

Potential applications include use of implanted cells in patients to monitor therapy prognosis (such as implanted stem cells that report on their differentiation in-vivo). Other applications could include modification of critical stem cells to monitor for degenerative or geriatric pathologies by continuous chronic detection of barcode levels (such as marking implanted progenitor cells with barcode for differentiation into beta cells to produce insulin and checking their differentiation over time).

The disclosure relates to a new in vivo or ex vivo transcript measurements using established CRISPR, Talen, Zinc-Finger or other genome editing technology to introduce a unique DNA barcode into a defined position of the genome of a cell. This barcode is expressed as a nonfunctional miRNA molecule, which is then packaged into vesicles and secreted. It can be detected with e.g., RT-PCR, miRNA sequencing and similar techniques.

Although the genome of the cell is modified, it is only minimally changed to include a barcode, which is a unique identifier that is typically fairly small (20-30 nt). Therefore, there are fewer concerns about the introduction of such small, nonfunctional sequences, as there are with disrupting protein-coding loci. Indeed, the human genome already has a substantial amount of such small noncoding sequences.

The disclosure includes any one or more of the following embodiments in any combination(s) thereof:

A method of determining an amount of transcript in a living organism, said method comprising: collecting secretions from a living organism that includes a DNA copy of a unique microRNA barcode downstream of a promoter of a transcript to be measured, such that expression of said transcript includes expression of said unique microRNA barcode; and measuring a level of said transcript by measuring an amount of said unique microRNA barcode in said secretions.

A method of determining an amount of transcript comprising: a) editing a genome of a cell to include a unique microRNA barcode downstream of a promoter of a transcript to be measured, such that expression of said transcript includes expression of said microRNA barcode, wherein said microRNA barcode is non-functional and is secreted out of said cell; b) collecting secretions from said cell; c) purifying microRNA barcodes from said secretions; d) measuring a level of said transcript by measuring an amount of said microRNA barcode.

A method of transcript tracking, comprising: a) editing a genome of a cell to include a unique microRNA barcode downstream of a promoter of a transcript to be measured, such that expression of said transcript includes expression of said microRNA barcode wherein said microRNA barcode is non-functional and is secreted out of said cell; b) culturing said cell in culture or in an animal in vivo; c) collecting secretions from said culture or said animal; d) purifying vesicular bodies from said secretions; e) purifying RNA from said vesicular bodies; f) amplifying said microRNA barcodes; and g) measuring a level of said transcript by measuring an amount of said amplified microRNA barcode.

A method of determining an amount of transcript in an animal or tissue comprising: a) editing a genome of a cell in an animal or tissue to include a DNA copy of a unique microRNA barcode downstream of a promoter of a transcript to be measured, such that expression of said transcript includes expression of said microRNA barcode, wherein said microRNA barcode is non-functional and is secreted out of said cell; b) collecting secretions from said animal or said tissue; c) purifying microRNA barcodes from said secretions; d) measuring a level of said transcript by measuring an amount of said microRNA barcode.

A method of determining an amount of transcript in an animal or tissue comprising: a) editing a genome of a cell in an animal or tissue to include a DNA copy of a unique microRNA barcode downstream of a promoter of a transcript to be measured, such that expression of said transcript includes expression of said microRNA barcode; b) extracting or collecting secretions from said animal or said tissue; c) purifying vesicular bodies from said secretions; d) purifying microRNA barcodes from said vesicular bodies; e) converting said microRNA barcodes to DNA barcodes and amplifying said DNA barcodes; and f) measuring a level of said transcript by measuring an amount of said amplified DNA barcode.

A method of determining an amount of a transcript in an animal comprising: a) editing a genome of a cell to include a unique microRNA barcode gene downstream of a promoter of a transcript to be measured, such that expression of said transcript includes expression of said microRNA barcode; b) transforming an animal with said cell; c) collecting secretions from said animal; d) purifying vesicular bodies from said secretions; e) purifying RNA including said microRNA barcodes from said vesicular bodies; f) converting said microRNA barcodes to DNA barcodes and amplifying said DNA barcodes; and g) estimating a level of said transcript by measuring an amount of said amplified DNA barcode. Usually, this is done with a standard curve prepared in advance or at the same time, as is known in the art.

A method of determining an amount of transcript in a living organism, said method comprising: editing a genome of a living organism to insert a DNA copy of a synthetic intron comprising a unique microRNA barcode with less than 15% homology to said genome downstream of a promoter of a transcript to be measured, such that expression of said transcript includes expression of said microRNA barcode; extracting secretions from said living organism; purifying microRNA barcodes from said secretions; converting said microRNA barcodes to DNA barcodes and amplifying said DNA barcodes; and, measuring a level of said transcript in said living organism by measuring an amount of said amplified DNA barcode. The microRNA is nonfunctional and cannot modulate expression of a gene in the host cell or species, but does contain all sequences needed for packaging and secretion.

Any method herein, wherein said living organism comprises two or more transcripts, each having a unique miRNA barcode therein.

Any method herein, wherein about 22-26, preferably about 24 nucleotides with minimal homology to said genome is inserted into a larger sequence of a preprocessed microRNA to form said miRNA barcode.

Any method herein, wherein said unique microRNA barcode originated from another species and has less than 10% homology to said genome.

Any method herein, wherein said unique microRNA barcode has less than 10% homology to said genome and is a random sequence or is a synthetically designed sequence.

Any method herein, said method further comprising selecting unique microRNA barcode sequences by screening against either against media conditioned by unmodified cells to be used for in vitro experiments or by sera from an animal with no barcoded cells to be used for in vivo experiments, wherein screening is performed by purifying vesicular bodies from said media or sera, purifying RNA from said vesicular bodies; amplifying said microRNA barcode sequences; and selecting those sequences that fail to produce an amplification product.

Any method herein described, wherein said cell or animal or tissues have two or more transcripts, each having a unique miRNA barcode therein.

Any method herein described, wherein said miRNA barcode includes motifs to expedite and increase efficiency of secretion, as described in Villarroya-Beltri (2013) and at systembio.com.

Any method herein described, wherein secretions include media, blood, lymphatic fluid, urine, mucus, and the like.

Any method herein described, wherein said editing step uses CRISPR-Cas or TALEN/ZFN.

An engineered cell made by any of the methods described herein, or made by editing a genome of a cell to include a unique microRNA barcode downstream of a promoter of a transcript of interest, such that expression of a plurality of said transcripts includes expression of a plurality of said microRNA barcodes, such that at least a portion of said microRNA barcodes are secreted from said cell in vesicular bodies.

An engineered stem cell made by the methods described herein.

An engineered tissue made by culturing the cells made hereunder in a 3D culture.

An engineered animal made by transforming an animal with a cell as described herein, wherein the cells is preferably a stem cell, and preferably autologous or syngeneic.

An engineered animal made by implanting an animal with the tissue made as described herein, wherein said tissue is preferably autologous or syngeneic. For example, heart valve or muscle tissue can be repaired using stems cells tagged with the barcodes of the invention.

Sequence data for many thousands of genomes and many hundreds of thousands of genes and proteins is available at ncbi.nlm.nih.gov/. Furthermore, there are also some 28645 entries of miRNA sequences available at mirbase.org/. Intron/exon databases are also available, see e.g. intron.ucsc.edu/yeast4.1/ or /omictools.com/exon-intron-database-tool or hsls.pitt.edu/obrc/index.php?page=URL1150311388.

The OMIN database is a good resource for searching human proteins and has links to the sequences. Further, every protein record is linked to a gene record, making it easy to design genome insertion vectors. Many sequences are already available in vectors, and can often be obtained from cell depositories or from the researchers who cloned them. But, if necessary, new clones can be prepared based on available sequence information using gene synthesis or PCR techniques. Thus, it should be easily possible to obtain all of the needed sequences.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence).

Alignments are performed using BLAST homology alignment as described by Tatusova T A & Madden T L (1999) FEMS Microbiol. Lett. 174:247-250. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 1 1 for proteins; E Cost to extend gap [Integer] default=2 for nucleotides, 1 for proteins; q Penalty for nucleotide mismatch [Integer] default=-3; r reward for nucleotide match [Integer] default=1; e expect value [Real] default=10; W word size [Integer] default=1 1 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs. This program is available online at NCBI™ (ncbi.nlm.nih.gov/BLAST/).

As used herein, the expressions "cell", "cell line" and "cell culture" are used interchangeably and all such designations include progeny. Thus, the words "cells" and similar designations include the primary subject cell and cultures derived therefrom without regard for the number of transfers. It is also understood that all progeny may not be precisely identical in DNA content, due to deliberate or inadvertent mutations or epigenetic changes that arise after genetic engineering is concluded. Mutant progeny that have the same function or biological activity (in this case, the same barcode and fluorescent marker) as screened for in the originally transformed cell are included. Where distinct designations are intended, it will be clear from the context.

As used herein, the expressions "tissue", includes 2D or 3D cultures of one or more cells types, wherein the culture as a whole exhibits some of the characteristics of an analogous tissue in animal.

The terms "operably associated" or "operably linked," as used herein, refer to functionally coupled nucleic acid sequences.

As used herein "recombinant" is relating to, derived from, or containing genetically "engineered" material. In other words, the genetic material of a cell was intentionally manipulated by the hand of man in some way.

As used herein, "native" or "endogenous" refers to being from the host species in question. Thus a native miRNA for a human cell will have originated the miRNA sequences from a human cell.

Although we discuss miRNA use herein, it is understood that in the genome, the DNA copy thereof is present, such that when transcribed the miRNA form is produced. Nevertheless, the gene or DNA copy may still be called miRNA herein for simplicity. This usage is standard e.g., when discussing rRNAs, and it is believed to be clear to a person of ordinary skill in art that the gene is DNA, and the miRNA is transcribed from the miRNA gene.

It is also understood that the secreted form of the miRNA barcode is a mature miRNA, although it is nonfunctional since it lacks homology to any endogenous sequences. In the genome, however, additional sequences needed to package and secrete the mature miRNA are present.

As used herein, "unique" means that the sequence is not naturally present in the organism before gene editing, although more than one copy of the unique miRNA barcode can be added to the organism (e.g., one on each chromosome, or multiple copies can be added to improve sensitivity).

As used herein, "dissimilar" sequences means that there is no cross-hybridization under high stringency conditions, and preferably very little (<15% or <10%) cross hybridization at moderate stringency.

As used herein, "genome editing" or similar expressions refers to the targeted changing of the genomic sequence, using any of the existing or future gene editing technologies.

As used herein, a "non-functional miRNA" is an miRNA molecule that does not function to modulate transcription, but nonetheless has all of the processing sequences needed for packaging and secretion.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, and the like.

The following abbreviations are used herein:

| ABBREVIATION | TERM |
|---|---|
| CT | X-ray/computed tomography |
| DSB | DNA double stranded break |
| FIAU | Fialuridine, or 1-(2-deoxy-2-fluoro-1-D-arabinofuranosyl)-5-iodouracil |
| GCV | Ganciclovir |
| GEED | genome editing with engineered nucleases |
| HR | homologous recombination |
| IVM | In vivo microscopy |
| NHEJ | nonhomologous end-joining |
| NMR | Nuclear magnetic resonance |
| PET | positron emission tomography |
| SPECT | single-photon emission computed tomography |
| TALEN | Transcription Activator-Like Effector Nucleases |
| US | ultrasound |
| ZFN | Zinc finger nucleases |
| miRNA | microRNA |
| PCR | Polymerase chain reaction |
| RT | Reverse transcriptase |
| nt | nucleotides |

BRIEF DESCRIPTION OF THE DRAWINGS

FIG. 3. Schematic of the detailed structure of the miRNA barcodes.

FIG. 4. Schematic illustrating the secretion of the miRNA barcode and their detection by qPCR.

FIG. 8. The current groups of engineered nucleases used for genomic editing.

FIG. 9. Zing finger nuclease systems.

DETAILED DESCRIPTION

Figure 1:
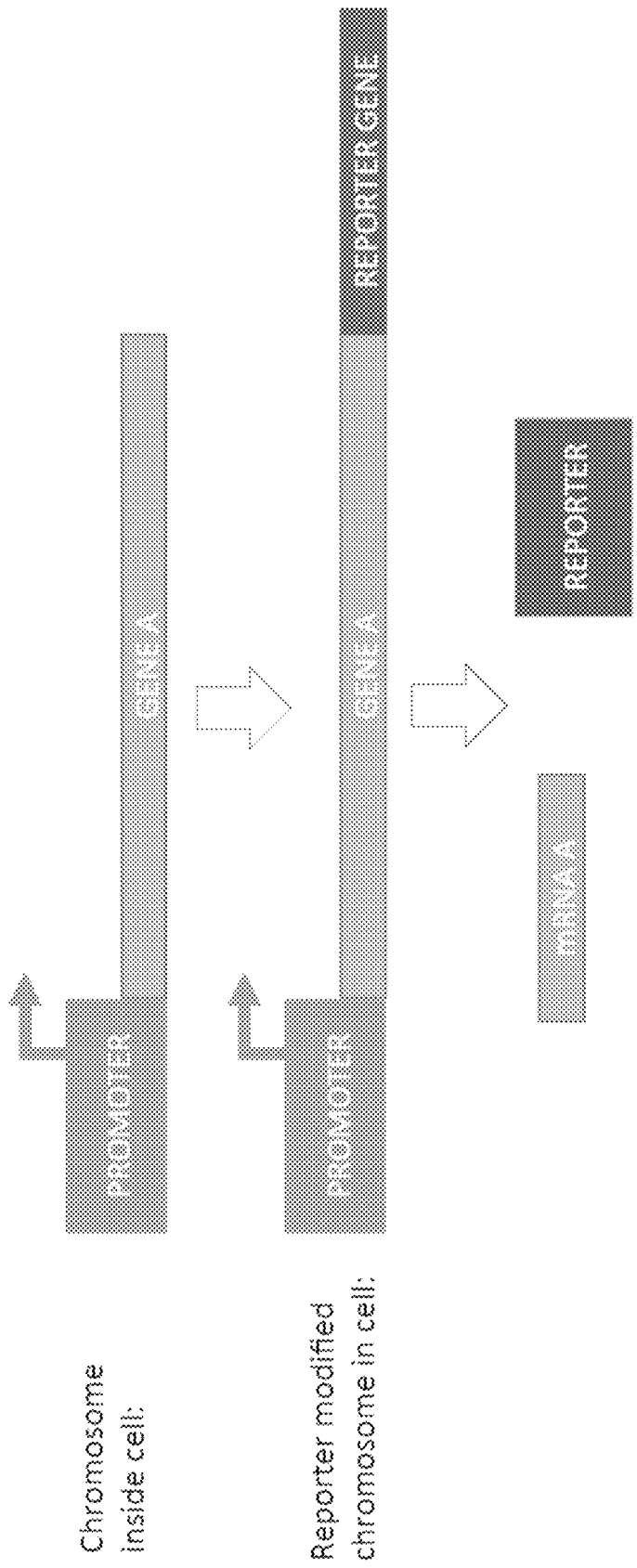
FIG. 1. General schematic of the use of reporters for expression of endogenous genes.

The disclosure provides novel genome editing and mRNA measurement techniques that allow one to assay transcripts in living cells or cell systems. For example, whether a particular marker of differentiation is induced when stem cells are used in cellular therapy. Such methods will be very important as we continue to develop gene and stem cell therapies for human use.

The invention is a composition of matter or article of manufacture in so far as the cells whose transcripts are to be non-invasively measured will have their genomes edited. The genome editing is accomplished via genome editing technologies such as CRISPR-Cas, TALEN/ZFN, piggybac etc.

The cells are edited to ensure the microRNA barcodes are downstream of the promoter responsible for transcribing the transcript to be measured. This ties the production of the barcode to the production of the transcript allowing for a correlative measure of the transcripts.

Limitations of our technology may include:

1. There is no spatial or single-cell level information as to the expression of transcripts (we do not know at what level single cells make transcripts or whether certain transcripts are made at certain spatial locations opposed to others).

2. The secretion of microRNA barcodes is probably not 100% and therefore not all the transcript-derived barcodes are available for detection. As long as the fraction of the barcode that is secreted does not change with experimental conditions, barcodes will still serve as a faithful reporter of gene expression. Particular sequences which have their secretion modulated by biological processes (e.g. by cellular differentiation) would not be less suitable to serve as reporters.

3. Cells must be engineered with a separate reporter for each process or transcript under study. Practically, this likely limits the number of transcripts reported on simultaneously to <100, although with advances in multiplexing technology, this may increase.

Modifications of the method could include:

1. Editing of cells to produce a constitutive microRNA that is unique to the cell and ubiquitously expressed in secreted vesicles (Cell ID barcode).

2. Droplet or single-cell RT-qPCR could be used to detect transcript barcodes and cell ID barcode simultaneously providing a single cell level information of transcripts.

3. Barcodes could be integrated in a site-specific manner via CRISPR-Cas, TALEN/ZFN etc., so that the barcode is solely present downstream of the coding sequence it reports on; at the rate of one (heterozygous) or two (homozygous) copies per cell. Barcodes could also be randomly integrated into the genome with multiple copies, which may aid in the detection of transcripts expressed at low levels. This could be achieved via transposable or other elements and placing the barcode downstream of a promoter binding element or whole promoter or an active part of the promoter, from the gene it is intended to report on.

Next, the method is described in more detail. First, barcodes are designed by picking about 24 base pairs of nucleic acids that have minimal homology to the human genome (or other genome of the organism under study). In preferred embodiments, the sequences can be from other species. In other embodiments, the sequences can be preselected for not binding to the genome of the host organism.

The 24 base pair barcode is inserted into a larger sequence of a pre-processed microRNA. The barcode can also incorporate motifs that are known to expedite and increase efficiency of secretion. Such motifs include the sequences GAGG and CCCU (Villarroya-Beltri, 2013).

This miRNA barcode (the DNA copy thereof) is then inserted by genome editing into the target transcript downstream of the promoter, in either 1) a position where it doesn't interfere with target expression, e.g., 3' to the protein coding sequence, or 2) in an intron. In preferred embodiments, an intron is inserted into the transcript with appropriate signals at either end to allow for correct transcript processing. The intron can thus be anywhere within the transcript, whereas otherwise the miRNA would need to be placed so as to not interfere with the coding sequences.

After genome editing, cells are cultured (e.g., in standard or 3D tissue cultures) or implanted in-vivo and their secretions are obtained (e.g., culture media, blood, urine, milk, lymph, etc.). The secretions are processed for isolation of vesicular bodies and the vesicular bodies are lysed for extraction of RNA. The microRNA is then conventionally extracted with commercial kits, the miRNA converted to DNA and then amplified for quantification via RT-qPCR or sequencing.

Initially, correlation experiments are conducted by measuring mRNA transcripts directly from cells while simultaneously measuring miRNA barcode expression to ascertain a linear relationship. This relationship will later allow for direct quantification of mRNA transcript levels in cells from measurement of barcodes. We have successfully performed such experiments, and can confirm that the method correlates well with cellular mRNA levels and with cellular luciferase levels.

By using CRISPR, TALEN or other genome editing technologies, we can stably integrate a unique barcode into a defined region of each cell's genome, somewhere downstream of a promoter of interest, such that the promoter not only provides expression of the transcript of interest, but also transcribes the miRNA, e.g., in an intron or somewhere not deleterious.

As our barcodes are synthetic and specifically designed to be highly dissimilar to the natural RNA produced by the cell, we can detect them with high signal to noise ratio. Use of site-specific genome editing technology also allows one-step integration of different barcodes into cells. This is because once a barcode integrates into the cell it modifies the genome preventing further integrations. If barcodes are incorporated together with a given antibiotic resistance gene to a specific site for integration, we can ensure only a single copy of that resistance gene bearing barcode is integrated into the cell, conserving the barcode scheme.

Besides use for research, in animal models and clinical trials, the technology will be vital for drug discovery, tissue engineering and development related diagnostics (cancer, aging, atrophy).

Variations on the methodology include choice of methods to introduce barcodes into host cells including lentiviral infection, liposome mediated transfection, and nucleofection. Various genome-editing system are available in systems to insert barcodes into the genome, including transposase elements, CRISPRs, TALENs, or zinc-finger nucleases, meganucleases, and the like. It is also expected that new genome editing techniques will continue to be developed, since this technology is proving to be extremely useful in research and development.

Genome editing, or genome editing with engineered nucleases (GEEN) is a type of genetic engineering in which DNA is inserted, replaced, or removed from a genome using artificially engineered nucleases, or "molecular scissors." The nucleases create specific double-stranded break (DSBs) at desired locations in the genome, and harness the cell's endogenous mechanisms to repair the induced break by natural processes of homologous recombination (HR) and non-homologous end-joining (NHEJ).

There are currently four families of engineered nucleases being used: Zinc finger nucleases (ZFNs), Transcription Activator-Like Effector Nucleases (TALENs), the CRISPR/Cas system, and engineered meganuclease re-engineered homing endonucleases.

First and foremost in understanding the use of nucleases in genome editing is the understanding of DNA double stranded break (DSB) repair mechanisms. Two of the known DSB repair pathways that are essentially functional in all organisms are the non-homologous end joining (NHEJ) and homology directed repair (HDR).

NHEJ uses a variety of enzymes to directly join the DNA ends in a double-strand break. In contrast, in HDR, a homologous sequence is utilized as a template for regeneration of missing DNA sequence at the break point. The natural properties of these pathways form the very basis of nucleases based genome editing.

NHEJ is error prone such that it was shown to cause mutations at the repair site in approximately 50% of DSB in mycobacteria and also its low fidelity has been linked to mutational accumulation in leukemias. Thus if one is able to create a DSB at a desired gene in multiple samples, it is very likely that mutations will be generated at that site in some of the treatments because of errors created by the NHEJ infidelity.

On the other hand, the dependency of HDR on a homologous sequence to repair DSBs can be exploited by inserting a desired sequence within a sequence that is homologous to the flanking sequences of a DSB which, when used as a template by HDR system, would lead to the creation of the desired change within the genomic region of interest.

Despite the distinct mechanisms, the concept of the HDR based gene editing is in a way similar to that of homologous recombination based gene targeting. However, the rate of recombination is increased by at least three orders of magnitude when DSBs are created and HDR is at work, thus making the HDR based recombination much more efficient and eliminating the need for stringent positive and negative selection steps. Based on these principles, if one is able to create a DSB at a specific location within the genome, then the cell's own repair systems will help in creating the desired mutations.

Creation of a DSB in DNA should not be a challenging task as the commonly used restriction enzymes are capable of doing so. However, if genomic DNA is treated with a particular restriction endonuclease many DSBs will be created. This is a result of the fact that most restriction enzymes recognize a few base pairs on the DNA as their target and very likely that particular base pair combination will be found in many locations across the genome. To overcome this challenge and create site-specific DSB, three distinct classes of nucleases have been discovered and bioengineered to date, and more are anticipated. These are the Zinc finger nucleases (ZFNs), transcription-activator like effector nucleases (TALENs) and meganucleases. Below is a brief overview and comparison of these enzymes and the concept behind their development.

Meganucleases, found commonly in microbial species, have the unique property of having very long recognition sequences (>14 bp) thus making them naturally very specific. This can be exploited to make site-specific DSB in genome editing; however, the challenge is that not enough meganucleases are known, or may ever be known, to cover very many possible target sequences. To overcome this challenge, mutagenesis and high throughput screening methods have been used to create meganuclease variants that recognize unique sequences. Others have been able to fuse various meganucleases and create hybrid enzymes that recognize a new sequence. Yet others have attempted to alter the DNA interacting amino acids of the meganuclease to design sequence specific meganucleases in a method named rationally designed meganuclease (see e.g., U.S. Pat. No. 8,021,867, incorporated by reference herein in its entirety for all purposes).

Meganucleases have the benefit of causing less toxicity in cells compared to methods such as ZFNs, probably as a result of their more stringent DNA sequence recognition. However, the construction of sequence specific enzymes for all possible sequences is costly and time consuming as one is not benefiting from combinatorial possibilities that methods such as ZFNs and TALENs utilize.

As opposed to meganucleases, the concept behind ZFNs and TALENs is more based on a non-specific DNA cutting enzyme, which would then be linked to specific DNA sequence recognizing peptides such as zinc fingers and transcription activator-like effectors (TALEs). The key to this was to find an endonuclease whose DNA recognition site and cleaving site were separate from each other, a situation that is not common among restriction enzymes. Once this enzyme was found, its cleaving portion could be separated, and would be very non-specific as it would have no recognition ability. This portion could then be linked to sequence recognizing peptides that could lead to very high specificity.

One restriction enzyme with such properties is FokI. Additionally FokI has the advantage of requiring dimerization to have nuclease activity and this means the specificity increases dramatically as each nuclease partner would recognize a unique DNA sequence. To enhance this effect, FokI nucleases have been engineered that can only function as heterodimers and have increased catalytic activity.

The heterodimer functioning nucleases avoid the possibility of unwanted homodimer activity and thus increase specificity of the DSB. Although the nuclease portion of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically happen in repeats that are 3 bp apart and are found in diverse combinations in a variety of nucleic acid interacting proteins such as transcription factors. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities.

Zinc fingers have been more established in approaches such as modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among other methods have been used to make site specific nucleases.

FIG. 1 shows a general schematic representing the use of a reporter gene to determine gene expression. The reporter is produced in a 1:1 stoichiometry with the mRNA to be measured.

Figure 2:
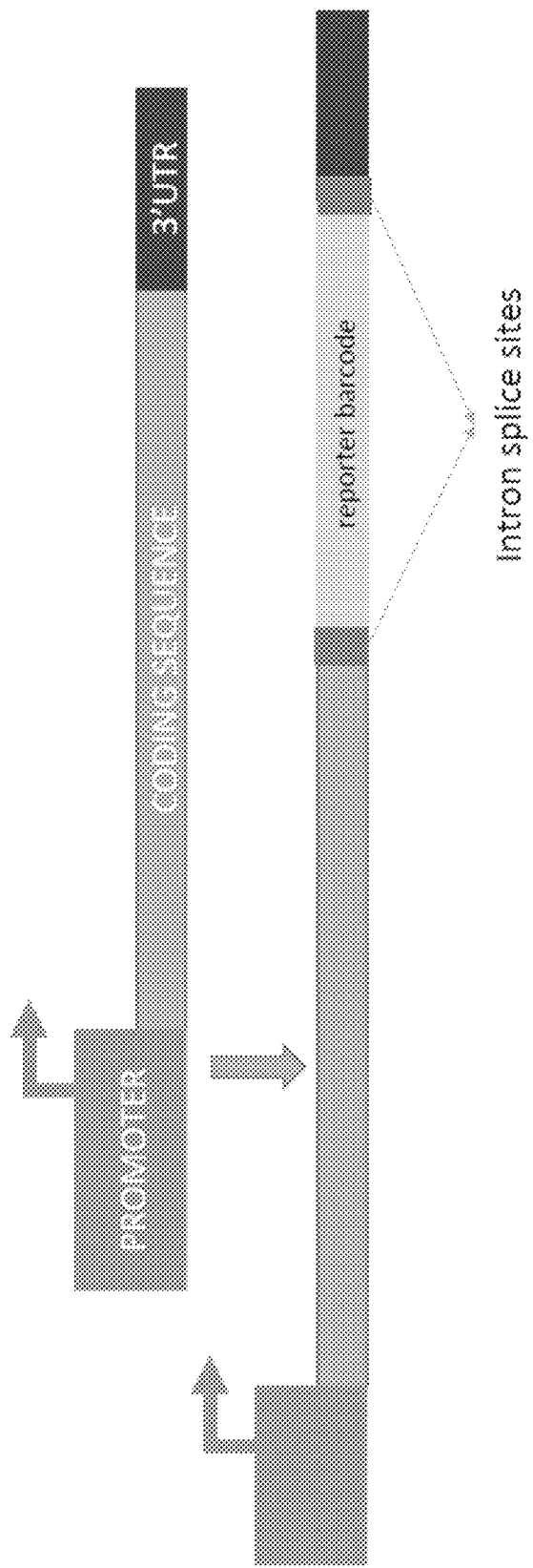
FIG. 2. Schematic demonstrating the incorporation of a miRNA barcode into an endogenous locus using a synthetic intron.

FIG. 2 shows a schematic representing the integration of a microRNA barcode into a genomic locus. A reporter barcode is integrated into a genomic locus of interest using genome engineering tools. Cells transcribe the barcode whenever they transcribe the upstream gene, and barcode is processed into microRNA. Intron splice sites (purple) allow for production of gene (blue) and reporter (yellow) in a constant proportion making the reporter effective. Adding a synthetic intron to the gene is preferred because it avoids unwanted complications that may arise from alternative splicing which may be biological regulated, and further allows standardization of processing between different barcodes so that they can be directly compared. However, the miRNA can also be added to an existing intron within a gene.

FIG. 3 shows the detailed structure of the microRNA reporter. The barcode is placed between splice sites (purple) and contains the microRNA barcode and the necessary machinery for cellular processing. The barcode is encoded in the antisense stem loop of the microRNA. The remainder of the sequence between the splice sites is necessary to produce and process the microRNA barcode reporter.

FIG. 4 is a schematic showing secretion of the microRNA reporter from modified cells and the detection of the reporter by qPCR. A cellular gene is expressed as an mRNA (yellow) and it's associated reporter as a microRNA (brown). The microRNA is exported out of the cell and is harvested from surrounding fluid and detected using RT-qPCR.

Figure 5:
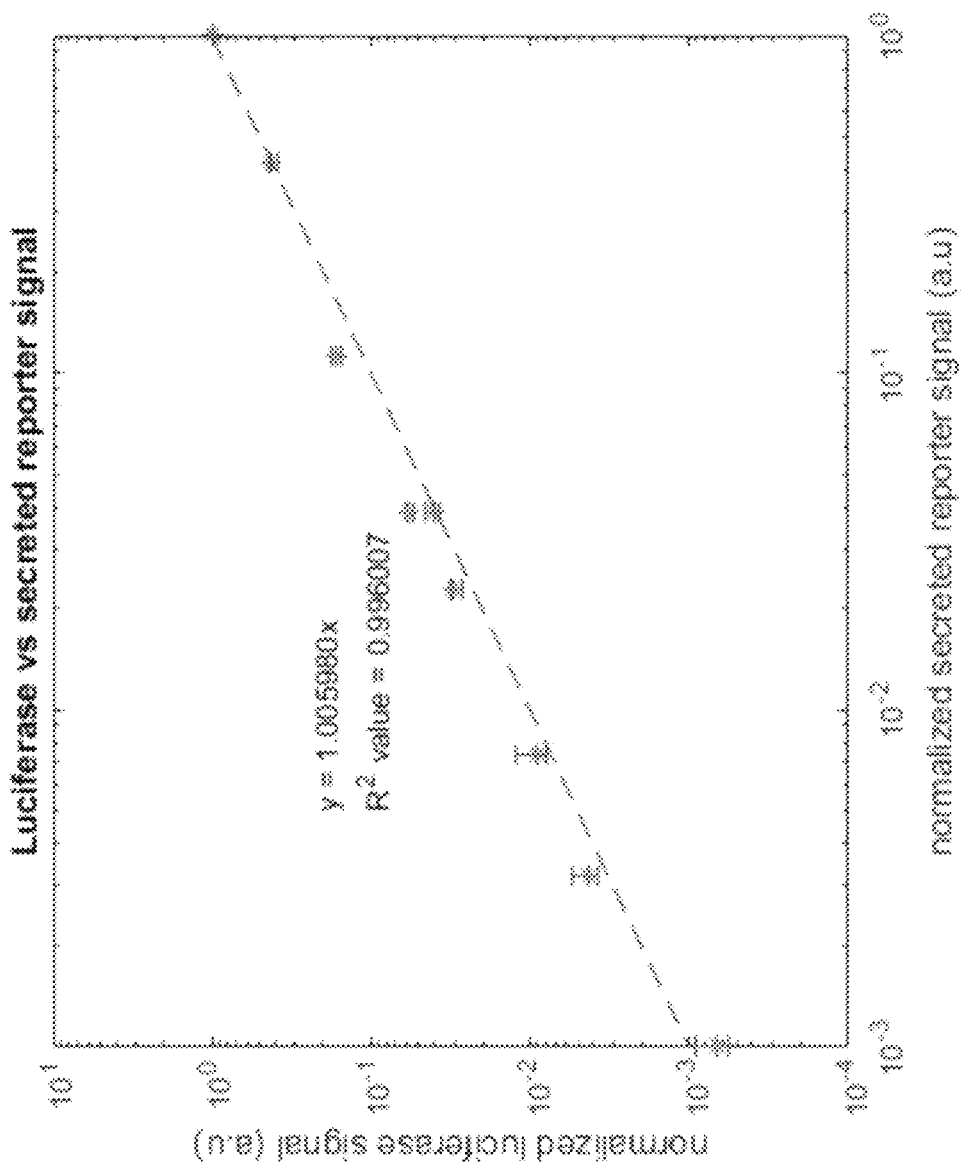
FIG. 5. Data from cancer cell line HEYA8 comparing luciferase (y axis) and miRNA (x axis) reporters. Stars reflect datapoints averaged over triplicate experiments, and bars show the extent of variance. The dashed line is the curve fitted to the data. As can be seen, both methods are directly comparable.

FIG. 5 shows comparison of luciferase and microRNA reporters. HeyA8 human ovarian cancer cells were modified to introduce the luciferase gene with a microRNA barcode downstream of luciferase in a synthetic intron. Modified cells were mixed with unmodified cells in ratios ranging from 0.1-100% modified cells, and both the luciferase signal from cell lysates and the barcode signal from the media were determined. Stars reflect datapoints averaged over triplicate experiments, and bars show the extent of variance. The dashed line is the curve fitted to the data. The results show an excellent correlation (R>0.99) between the luciferase and the secreted microRNA signals, with nearly identical fold changes between samples (slope of best fit line 1.01).

Figure 6:
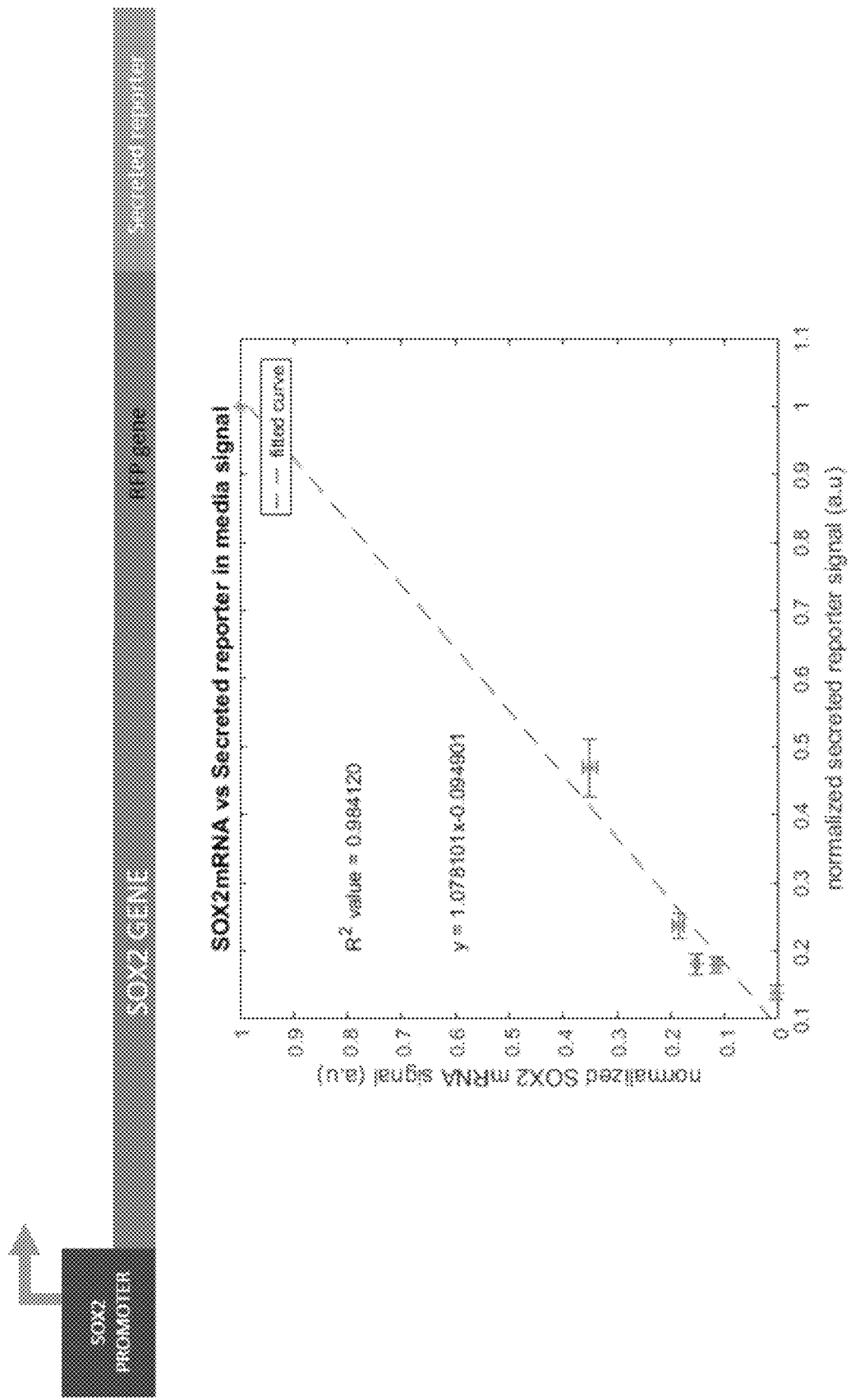
FIG. 6. Data from human embryonic stem cells showing the use of a secreted reporter for measuring expression of Sox2, a key pluripotency-associated gene. The figure compares mRNA levels inside the cells (y axis) with miRNA secreted into the media (x axis). Stars reflect datapoints averaged over triplicate experiments, and bars show the extent of variance. The dashed line is the curve fitted to the data. As can be seen, both methods are directly comparable, although the barcode method is applicable to live cells, whereas mRNA extraction lyses the cells, preventing further work.

FIG. 6 shows the use of a secreted reporter to determine the expression of Sox2, a key pluripotency associated gene, in human embryonic stem cells. A red fluorescent protein (RFP) sequence with a synthetic intron containing the miRNA barcode reporter was integrated at the endogenous Sox2 locus downstream of the Sox2 coding sequence. Reporter cells were treated with concentrations of BMP4 ranging from 0-100 ng/ml, which induces differentiation and suppresses Sox2 expression in a dose-dependent manner. In each case, media was collected to determine secreted barcode expression, and the amount of Sox2 mRNA was determined from cell lysates. Stars reflect datapoints averaged over triplicate experiments, and bars show the extent of variance. The dashed line is the curve fitted to the data. The results show an excellent correlation between Sox2 mRNA expression and barcode as measured from the media (R=0.98) with nearly identical fold changes in the mRNA and reporter (slope of best fit line 1.07).

Figure 7:
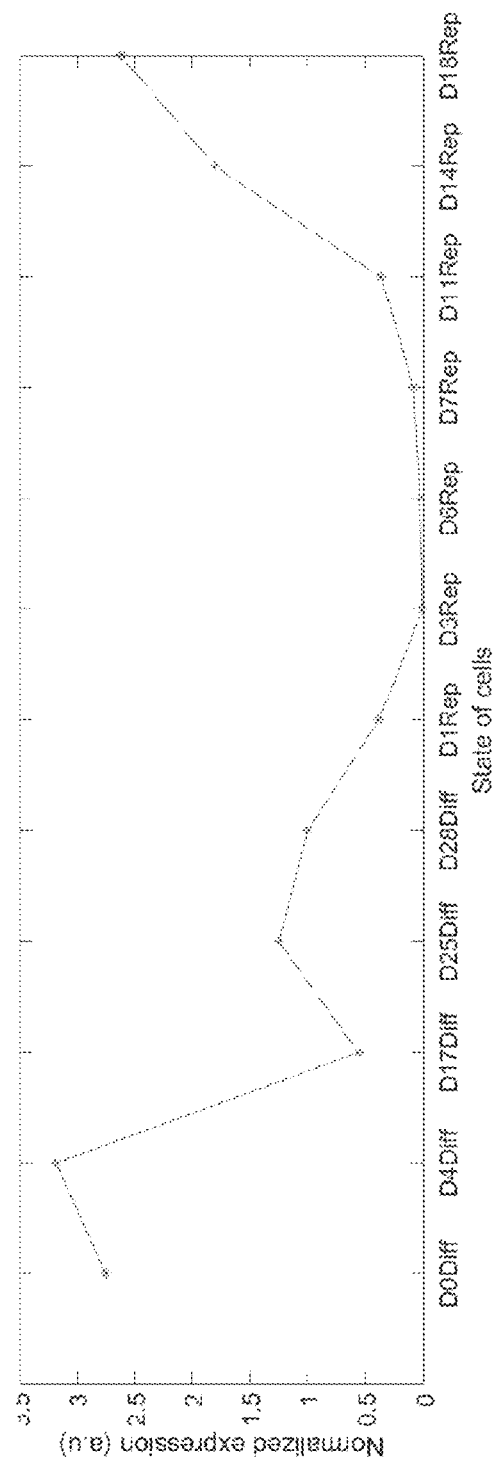
FIG. 7. Shows the use of the Sox2 miRNA secreted reporter to follow the processes of differentiation and reprogramming to pluripotency. Cells were differentiated to fibroblast lineages for 28 days and then reprogrammed using a protocol based on introducing reprogramming factors with Sendai virus. Reporter expression declines during differentiation and is restored during reprogramming. The x-axis shows the time points (e.g. DXDiff indicates the number of days of differenation, DXRep indicates the number of days of reprogramming). The y-axis shows the amount of the miRNA barcode as measured from the culture media.

FIG. 7 shows the use of a secreted barcode to monitor cellular differentiation and reprogramming. Sox2 reporter cells (see FIG. 6) were first differentiated into fibroblasts lineages for 28 days and then the fibroblasts were reprogrammed to induced pluripotent stem cells using a strategy based on introducing pluripotency factors with Sendai virus. The number of days of differenation or reprogramming is shown on the x-axis while the expression of the Sox2 reporting barcode as determined from the culture media is shown on the y-axis. The Sox2 reporter is suppressed during differentiation and reactivated upon reacquisition of pluripotency.

FIGS. 8 and 9 show some of the enzymes that could be used in the various gene editing methodologies known in the art, but additional enzymes are being developed all the time.

Figure 10:
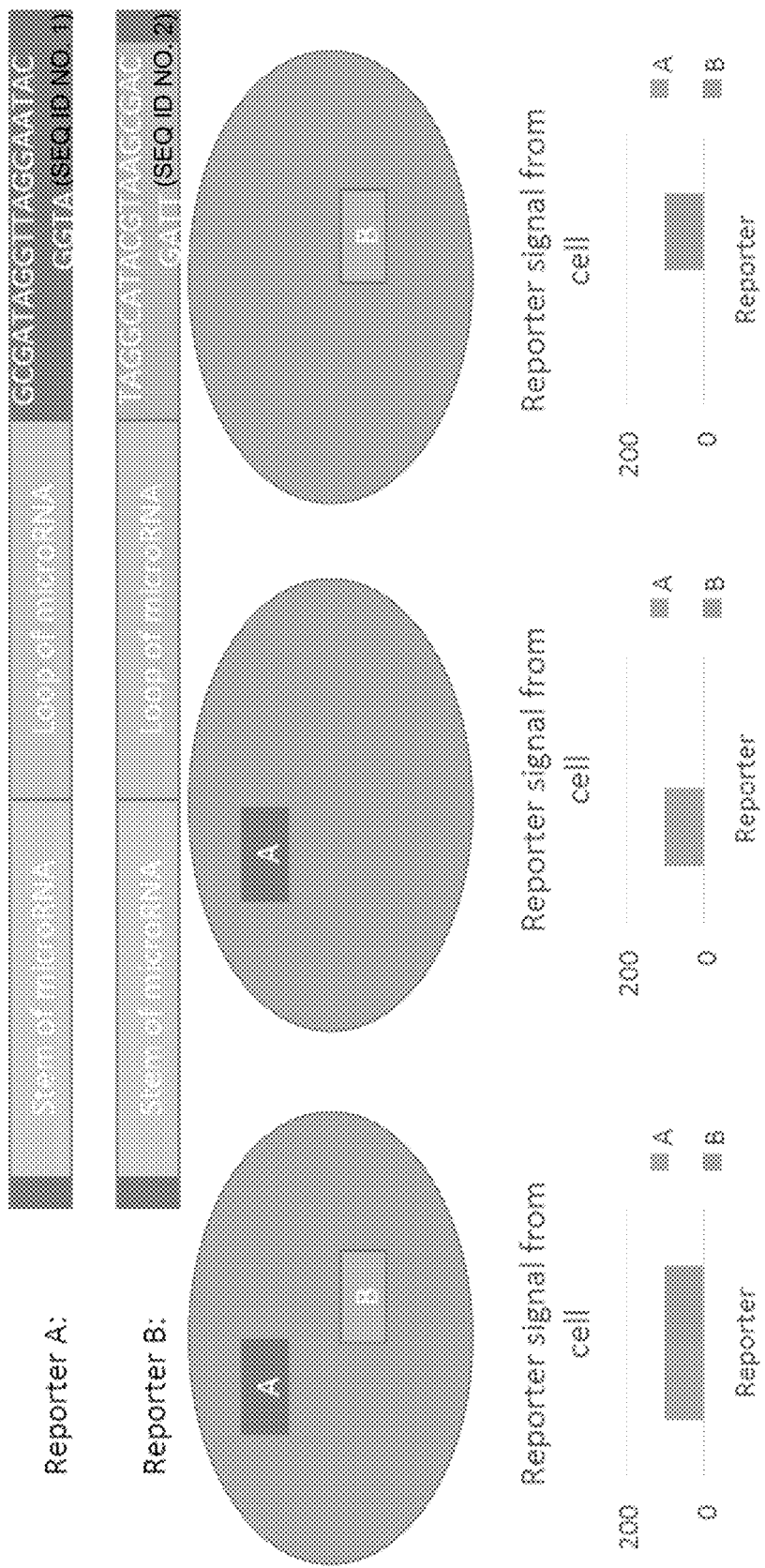
FIG. 10. Schematic of a proposed experiment demonstrating the use of multiplexed barcodes to report on multiple gene simultaneously.

FIG. 10 shows a planned experiment to demonstrate the multiplexibility of the reporter system. Two different barcodes will be integrated into the genome to report on two different genes. Cells expressing only a single one of these genes are expected to only secrete its corresponding reporter to the cell media while cells expressing both genes are expected to secrete both reporters.

Figure 11:
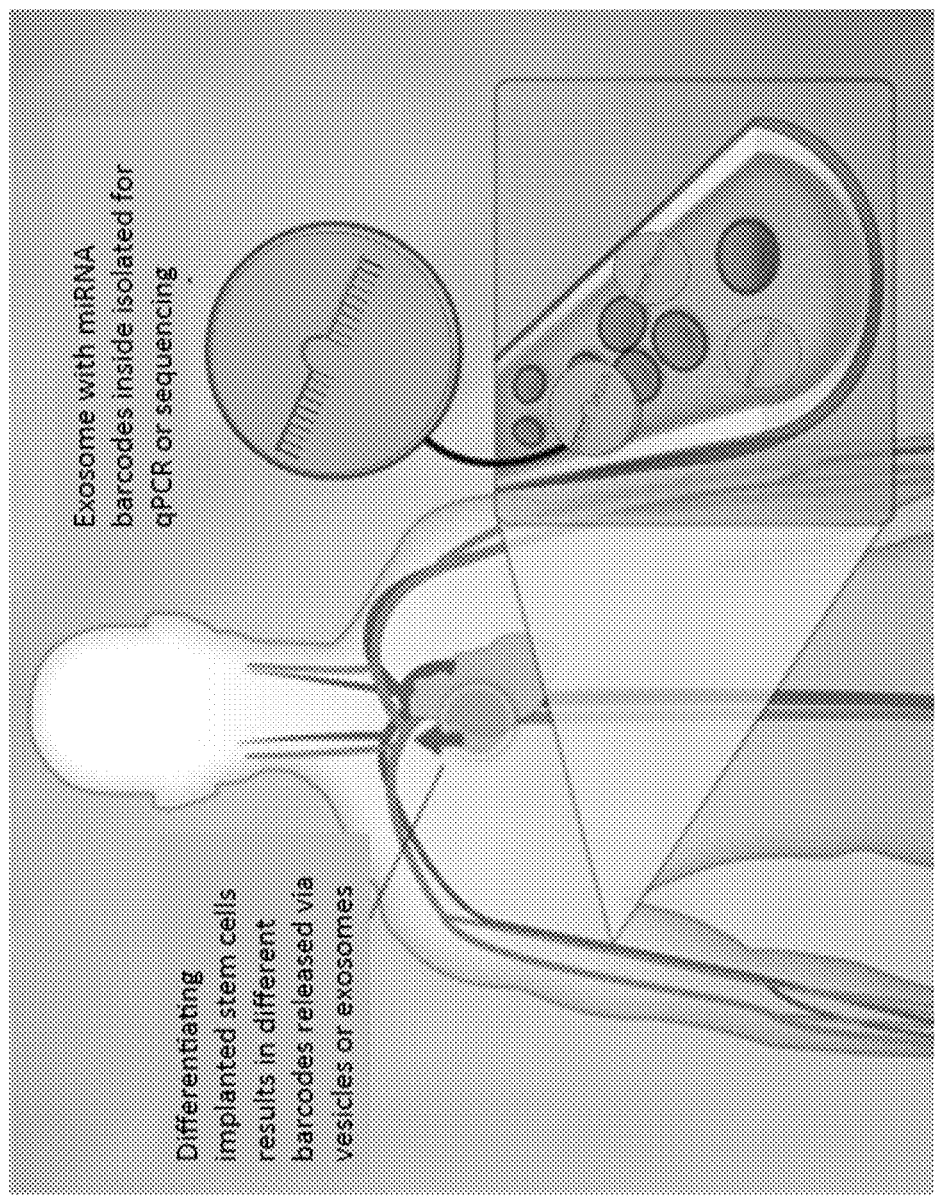
FIG. 11. Schematic of the use of barcodes to report on the behavior of cells inside an organism.

FIG. 11 illustrates the use of barcoded cells when implanted in an organism. MicroRNA barcodes from the cells are secreted and can be detected in fluids such as the blood and urine.

Experiments are currently underway to demonstrate the use of the barcodes in vivo in mice. Cancer cells that have been modified to constitutively express luciferase with a miRNA barcode in a synthetic intron are injected into immuno-compromised mice. Every week for 4 weeks, we will perform bioluminescent imaging of the mice to determine the amount of luciferase expressing cells within the resulting tumors, and extraction of blood and peritoneal fluids to determine the expression of the secreted miRNA reporter in these fluids. We predict a strong correlation between the luciferase signal and the barcode signals from the fluids demonstrating the use of the barcodes as a reporter of cell numbers in vivo.

We also plan to engineer cancer cells to express luciferase and a barcode downstream of the promoter of an endogenous gene, for example, the Snail gene, that is indicative of cells that have undergone an epithelial to mesenchymal transition, a crucial step in metastasis. We again predict a strong correlation between luciferase activity and barcode expression measured from blood, urine, or other fluids, thus validating the use of the barcodes in measuring gene expression and reporting on cellular events in vivo.

The above descriptions are exemplary only and not intended to unduly limited the scope of the claims.

The following references are incorporated by reference in their entirety for all purposes.

Bovenberg, M. S. S., et al. "Multiplex blood reporters for simultaneous monitoring of cellular processes." Analytical Chemistry 85(21): 10205-10210 (2013).

Chen, X., et al., "Characterization of microRNAs in serum: a novel class of biomarkers for diagnosis of cancer and other diseases," Cell Research 18:997-1006 (2008).

Corrêa, I. R. "Live-cell reporters for fluorescence imaging." Current Opinion in Chemical Biology 20:36-45 (2014).

Esvelt, K. M., and Harris H. W. "Genome-scale engineering for systems and synthetic biology." Molecular Systems Biology 9: 641 (2013).

Fellmann, C., et al. "An optimized microRNA backbone for effective single-copy RNAi'." Cell Reports 5(6):1704-1713 (2013).

Gonzalez-Martin, A., et al., "The microRNA miR-148a functions as a critical regulator of B cell tolerance and autoimmunity," Nature Immunology 17(4): 433-442 (2016).

Heneghan H. M., et al., "Systemic miRNA-195 Differentiates Breast Cancer from Other Malignancies and Is a Potential Biomarker for Detecting Noninvasive and Early Stage Disease," The Oncologist 15:673-682 (2010).

Horwitz, R., "Integrated, multi-scale, spatial-temporal cell biology—A next step in the post genomic era." Methods 96:3-5 (2015).

Maeder, M. L., and Gersbach, C. A. "Genome Editing Technologies for Gene and Cell Therapy." Molecular Therapy 24(3): 430-436 (2016).

Qiu, L., et al. "A construct with fluorescent indicators for conditional expression of miRNA." BMC Biotechnology 8: 77 (2008).

Shapiro, M. G., et al. "Genetically encoded reporters for hyperpolarized xenon magnetic resonance imaging." Nature Chemistry 6: 629-634 (2014).

Shu, J., et al., "Computational Characterization of Exogenous MicroRNAs that Can Be Transferred into Human Circulation," PLoS ONE 10(11): e0140587 (2015).

Skotland, T., "Molecular imaging: challenges of bringing imaging of intracellular targets into common clinical use." Contrast Media & Molecular Imaging 7(1): 1-6 (2012).

Valadi, Hadi, et al. "Exosome-mediated transfer of mRNAs and microRNAs is a novel mechanism of genetic exchange between cells." Nature Cell Biology 9.6 (2007): 654-659.

Villarroya-Beltri, Carolina, et al. "Sumoylated hnRNPA2B1 controls the sorting of miRNAs into exosomes through binding to specific motifs." Nature Communications 4 (2013).

Xmotif System Biosciences Inc at systembio.com

The invention claimed is:

1. A method of determining an amount of transcript in a living organism, said method comprising:
   a) editing a genome of a living organism to contain a unique microRNA barcode;
   b) collecting secretions from said living organism that includes a DNA copy of said unique microRNA barcode downstream of a promoter of a transcript to be measured, such that expression of said transcript includes expression of said unique microRNA barcode; and
   c) measuring a level of said transcript by measuring an amount of said unique microRNA barcode in said secretions.

2. The method of claim 1, wherein editing step requires inserting a synthetic intron into said transcript to be measured, said synthetic intron comprising said miRNA barcode.

3. The method of claim 1, wherein said living organism includes two or more transcripts, each having said unique miRNA barcode therein.

4. The method of claim 1, wherein about 22-26 nucleotides with minimal homology to said genome is inserted into a larger sequence of a pre-processed microRNA to form said unique miRNA barcode.

5. The method of claim 1, wherein said unique microRNA barcode originated from another species and has less than 15% homology to a genome of said living organism.

6. The method of claim 1, wherein said unique microRNA barcode has less than 15% homology to a genome of said living organism and is a random sequence or is a synthetically designed sequence.

7. The method of claim 1, including selecting unique microRNA barcode sequences by screening either against media conditioned by unmodified cells to be used for in vitro experiments or by sera from an animal with no barcoded cells to be used for in vivo experiments, wherein screening is performed by purifying vesicular bodies from said media or sera; purifying RNA from said vesicular bodies; amplifying said microRNA barcode sequences; and selecting those sequences that fail to produce an amplification product.

8. The method of claim 1, wherein secretions include media, blood, lymphatic fluid, urine, or mucus.

9. The method of claim 1, wherein said editing step uses CRISPR-Cas or TALEN/ZFN.

10. A method of determining an amount of transcript in a living organism, said method comprising:
   a) editing a genome of a living organism to insert a DNA copy of a synthetic intron comprising a unique microRNA barcode with less than 15% homology to said genome downstream of a promoter of a transcript to be measured, such that expression of said transcript includes expression of said microRNA barcode, wherein said microRNA barcode is nonfunctional and is not intended to modulate expression of any gene in said living organism;
   b) extracting secretions from said living organism;
   c) purifying RNA from said secretions;
   d) converting said microRNA barcodes in said RNA to DNA barcodes and amplifying said DNA barcodes; and,
   e) measuring a level of said transcript in said living organism by measuring an amount of said amplified DNA barcode.

11. The method of claim 10, wherein said living organism comprises two or more transcripts, each having a unique miRNA barcode therein.

12. The method of claim 10, wherein about 22-26 nucleotides with minimal homology to said genome is inserted into a larger sequence of a pre-processed microRNA to form said miRNA barcode.

13. The method of claim 10, wherein said unique microRNA barcode originated from another species and has less than 10% homology to said genome.

14. The method of claim 10, wherein said unique microRNA barcode has less than 10% homology to said genome and is a random sequence or is a synthetically designed sequence.

15. The method of claim 10, said method further comprising selecting unique microRNA barcode sequences by screening either against media conditioned by unmodified cells to be used for in vitro experiments or by sera from an animal with no barcoded cells to be used for in vivo experiments, wherein screening is performed by purifying vesicular bodies from said media or sera, purifying RNA from said vesicular bodies; amplifying said microRNA barcode sequences; and selecting those sequences that fail to produce an amplification product.

16. The method of claim 10, wherein secretions include media, blood, lymphatic fluid, urine, or mucus.

17. The method of claim 10, wherein said living organism is cells and wherein said secretions are in media in which said cells were grown.

18. The method of claim 10, further comprising isolating vesicular bodies from said secretions and purifying RNA from said vesicular bodies.

19. The method of claim 10, wherein said unique microRNA barcode is within a nonfunctional microRNA having sequences for microRNA processing or sequences for packaging and secretion in vesicular bodies.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Barcode sequence

<400> SEQUENCE: 1
gcgataggtt aggaatacgg ta                                            22

<210> SEQ ID NO 2
<211> LENGTH: 22
<212> TYPE: DNA
<213> ORGANISM: Artificial Sequence
<220> FEATURE:
<223> OTHER INFORMATION: Barcode sequence

<400> SEQUENCE: 2
taggcatacg taagcgacga tt                                            22

<210> SEQ ID NO 3
<211> LENGTH: 33
<212> TYPE: DNA
<213> ORGANISM: Artificial Sequence
<220> FEATURE:
<223> OTHER INFORMATION: Target sequence

<400> SEQUENCE: 3
agcacagatt ccgaatcgat atcagaaagc ttt                                33

<210> SEQ ID NO 4
<211> LENGTH: 33
<212> TYPE: DNA
<213> ORGANISM: Artificial Sequence
<220> FEATURE:
<223> OTHER INFORMATION: Nuclease target sequence

<400> SEQUENCE: 4
aaagctttct gatatggatt cggaatctgt gct                                33
```